(12) United States Patent
Hsiao et al.

(10) Patent No.: US 12,281,998 B2
(45) Date of Patent: Apr. 22, 2025

(54) BIO-DETECTOR DEVICE FOR BIO-TARGETS

(71) Applicant: Taiwan Semiconductor Manufacturing Company, Ltd., Hsinchu (TW)

(72) Inventors: Yi-Hsing Hsiao, Hsinchu (TW); Jui-Cheng Huang, Hsinchu (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 892 days.

(21) Appl. No.: 17/140,306

(22) Filed: Jan. 4, 2021

(65) Prior Publication Data

US 2021/0372962 A1 Dec. 2, 2021

Related U.S. Application Data

(60) Provisional application No. 63/030,947, filed on May 28, 2020.

(51) Int. Cl.
*G01N 27/327* (2006.01)
*A61B 5/145* (2006.01)

(52) U.S. Cl.
CPC ..... *G01N 27/3272* (2013.01); *A61B 5/14546* (2013.01); *G01N 27/3273* (2013.01); *G01N 27/3275* (2013.01)

(58) Field of Classification Search
None
See application file for complete search history.

(56) References Cited

U.S. PATENT DOCUMENTS

| 9,958,443 B2 | 5/2018 | Lin et al. |
| 2007/0189931 A1* | 8/2007 | Ruhe ............... G01N 27/4143 422/88 |
| 2017/0227533 A1 | 8/2017 | Lin et al. |

(Continued)

FOREIGN PATENT DOCUMENTS

| TW | 200405933 | 4/2004 |
| TW | 201732285 | 9/2017 |

(Continued)

OTHER PUBLICATIONS

Analytical Electrochemistry: The Basic Concepts, B. Reference and auxiliary electrodes; accessed Nov. 12, 2023 from https://www.asdlib.org/onlineArticles/ecourseware/Kelly_Potentiometry/PDF-15-Ref&AuxElec.pdf (Year: 2023).*

(Continued)

*Primary Examiner* — J. Christopher Ball
(74) *Attorney, Agent, or Firm* — Jones Day

(57) ABSTRACT

Devices, methods for fabricating said devices, and methods for detecting an analyte within a bio-target are described herein. The device includes a top assembly and a bottom assembly. The Top assembly includes an electrode disposed on a top layer. The bottom assembly includes a bio-chip disposed on a bottom layer and a polymer body disposed between the bio-chip and the top assembly. The polymer body includes a channel. The electrode of the top assembly is positioned within the channel. The channel is configured to accommodate the bio-target containing the analyte.

20 Claims, 13 Drawing Sheets

(56) References Cited

U.S. PATENT DOCUMENTS

2017/0295988 A1    10/2017    Chung

FOREIGN PATENT DOCUMENTS

TW          201928343       7/2019
TW          202004177       1/2020

OTHER PUBLICATIONS

T.L. Edwards, et al., "A parallel microfluidic channel fixture fabricated using laser ablated plastic laminates for electrochemical and chemiluminescent biodetection of DNA", Biomicrofluidics, 5(4): paper 044115, 14 pages, Dec. 2011.*
C.-P. Hsu, et al., "A Package Technology for Miniaturized Field-Effect Transistor-Based Biosensors and the Sensor Array", ECS Journal of Solid State Science and Technology, 6(5): p. Q63-Q67, Apr. 2017.*
Taiwanese Office Action; Application No. 110106726; Dated Jul. 13, 2022.
Korean Office Action; Application No. 10-2021-0029572; dated Mar. 31, 2023.

* cited by examiner

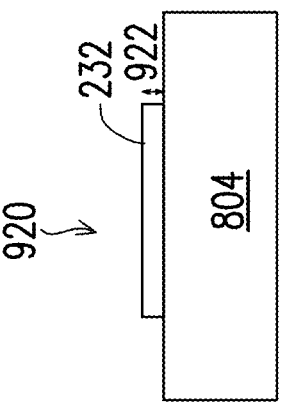

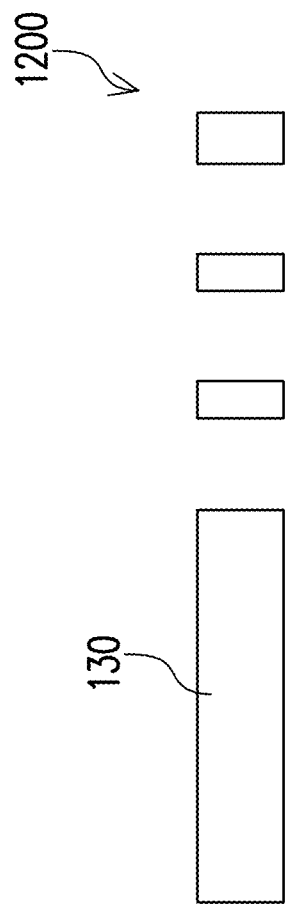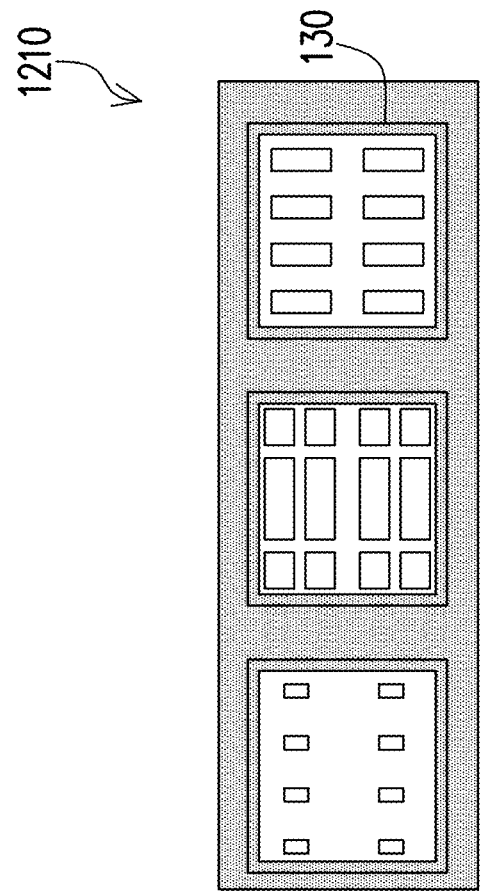
FIG. 12A
FIG. 12B

BIO-DETECTOR DEVICE FOR BIO-TARGETS

PRIORITY CLAIM

This application claims priority to U.S. Provisional Application No. 63/030,947 filed May 28, 2020, the contents of which are incorporated by reference herein in its entirety.

TECHNICAL FIELD

This application relates to generally to electrical devices and more specifically to detector devices for detecting bio-targets.

BACKGROUND

Clinics and hospitals worldwide utilize cell concentration to determine the health of a patient as it can provide diagnostic information and/or indicate medical conditions. Precise determination of cells in a sample can be important for a broad field of applications, such as micro-tissue culture studies by microbiologists and/or disease progression studies in medical laboratories. There are a number of different ways to determine a number of cells in a sample such as manual counting utilizing a hemocytometer, use of an impedance system such as a Coulter counter technology using a benchtop and handheld device, and/or use of an optical system such as optical flow cytometry.

BRIEF DESCRIPTION OF THE DRAWINGS

Aspects of the present disclosure are best understood from the following detailed description when read with the accompanying figures.

FIG. 9A illustrates a cross-sectional view of reference electrode in accordance with various embodiments of the present disclosure.

FIG. 9B illustrates another cross-sectional view of reference electrode in accordance with various embodiments of the present disclosure.

FIG. 9C illustrates another cross-sectional view of reference electrode in accordance with various embodiments of the present disclosure.

FIG. 9D illustrates another cross-sectional view of reference electrode in accordance with various embodiments of the present disclosure.

FIG. 12A illustrates a side view of a silicon polymer body in accordance with various embodiments of the present disclosure.

FIG. 12B illustrates a top view of a silicon polymer body in accordance with various embodiments of the present disclosure.

DETAILED DESCRIPTION

Figure 1:
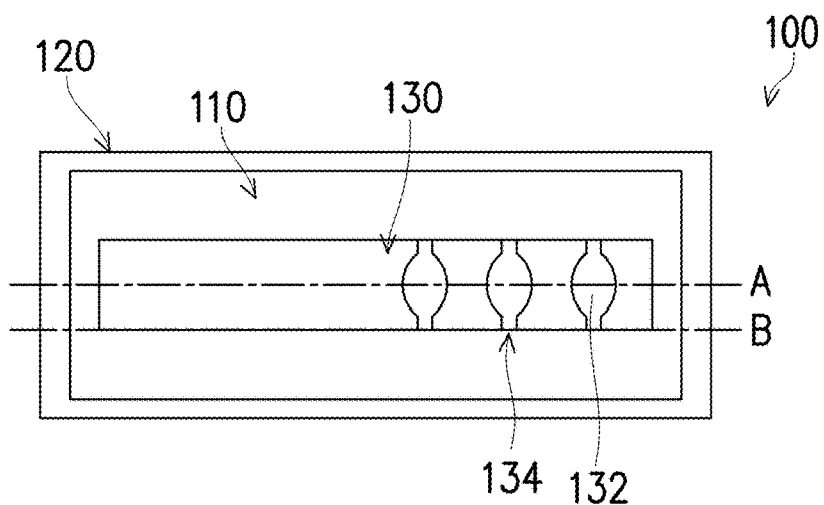
FIG. 1 illustrates a top view of an example bio-detector device in accordance with various embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

A bio-detector device is described herein that acts as a resistive sensor to detect and identify various size bio-targets, in embodiments, such as atoms, lipids, proteins, cells, bacteria, virus, deoxyribonucleic acid (DNA), proteins, and/or embryonic bodies. Detection of bio-targets can, for example, be utilized in drug screenings and/or point-of-care diagnostics. Resistive sensors can measure an electrical change within a particular substance under test. In relation to bio-target devices, a sample of the bio-target can be placed within or passed through an open space or channel within the bio-detector device. Once the bio-target sample is within the bio-detector device, a voltage is applied to the device and electrical changes within that sample are measured. The open space or channel can be adjusted in height to facilitate various sized bio-targets. For example, the resolution width of the resistive sensors may depend on the translocation speed and amplitudes may depend on the volume of the bio-target, thus allowing extracting the size of the bio-target. Utilizing the measured electrical changes along with the adjusted height of the channel, the bio-target sample can be detected and characteristics identified. Methods of fabricating the bio-detector device are also described herein.

FIG. 1 illustrates a top view 100 of an example bio-detector device in accordance with various embodiments of the present disclosure. Visible from top view 100, the bio-detector includes a bio-MOSFET chip 110, a perimeter layer 120, and a silicon polymer body 130. The silicon polymer body 130 can be made of any silicon polymer. In one example, silicon polymer body 130 is polydimethylsiloxane (PDMS). The silicon polymer body 130 includes a number of reservoirs or channels 132. The bio-target under test can be placed into the channel 132. IA height of the channel 132 is variable and can be adjusted based on the type of bio-target being tested for, as described in more detail in FIG. 2. In some embodiments, the bio-target under test is a liquid sample (e.g., blood or bodily fluid). The channels 132 includes vents 134 that facilitate bubbling of the bio-target once placed within the channel 132. Perimeter layer 120 can enclose the bio-detector device. Depending upon the positioning of perimeter layer 120, perimeter layer 120 can be any of a printed circuit board (PCB), glass, acrylic, or Poly(methyl methacrylate) (PMMA) as described in more detail in FIG. 2.

Figure 2:
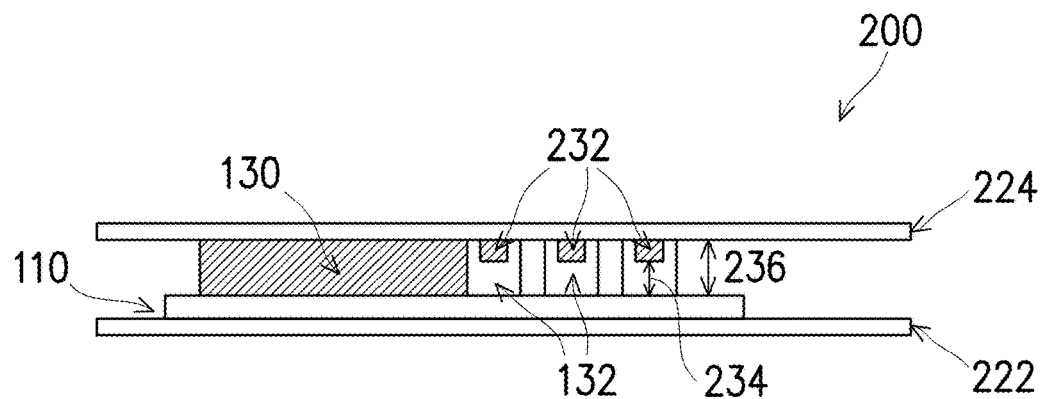
FIG. 2 illustrates a side view of an example bio-detector device along cross-section "A" annotated in FIG. 1 in accordance with various embodiments of the present disclosure.

FIG. 2 illustrates a side view 200 of an example bio-detector device along cross-section "A" annotated in FIG. 1 in accordance with various embodiments of the present disclosure. Visible from side view 200, the bio-detector device includes a bio-MOSFET chip 110, a silicon polymer body 130, reference electrodes 232, a bottom layer 222, and a top layer 224. Bottom layer 222 and top layer 224 of side view 200 together form the perimeter layer 120 illustrated in top view 100 of FIG. 1. The bio-MOSFET chip 110 is positioned a bottom layer 222, which is made upon PCB in accordance with some embodiments. Top layer 224 can be made up of any of PCB, glass, or PMMA. The silicon polymer body 130 is positioned between the bio-MOSFET chip 100 and the top layer 222. One or more channels 132 are formed within silicon polymer body 130 to facilitate testing of bio-targets or any other substance places within the channels 132, as described in more detail in FIGS. 12A-12B. Reference electrodes are coupled to the top layer 224 and positioned within the channels 132, the formation of which is described in more detail in FIGS. 8A-8D. The distance or height 234 between a surface of the bio-MOSFET 110 and reference electrodes 232 can be adjusted according to the specific bio-target(s) being tested. Those bio-targets can include, for example, atoms, lipids, proteins, cells, bacteria, virus, DNA, proteins, and/or embryonic bodies and range in relative size from 0.1 nm to 1 mm on a logarithmic scale (e.g., atom≈0.1 nm, C60≈1 nm, lipids≈3 nm, protein≈8 nm, flu virus≈100 nm, bacteria or mitochondria≈1 μm, red blood cell≈7 μm, animal or plant cells≈10μ to 100 μm, pollen or human egg≈300 μm, or frog egg≈1 mm). The ratio between the bio-target size and the height 234 between the reference electrode 232 and a surface of the bio-MOSFET 110 is approximately 2:3. In some embodiments, the height 234 between the surface of the bio-MOSFET 110 and the reference electrode 232 is adjusted by modifying a thickness of the reference electrode 232. The thickness of reference electrode 232 can range between 500 μm to 2 mm. The reference electrode can include materials such as gold (Au), platinum (Pt), silver (Ag), silver chloride (AgCl), or any combination thereof. In other embodiments, the height 234 between the surface of the bio-MOSFET 110 and the reference electrode 232 is adjusted by modifying the thickness 236 of the silicon polymer body 130, which can range between 2.01 mm to 3 mm (e.g., 2.01 mm, 2.1 mm, 2.2 mm, 2.3 mm, 2.4 mm, 2.5 mm). In yet other embodiments, the height 234 between the surface of the bio-MOSFET 110 and the reference electrode 232 is adjusted by a combination of modifying the thickness of both the reference electrode 232 and the silicon polymer body 130.

Figure 3:
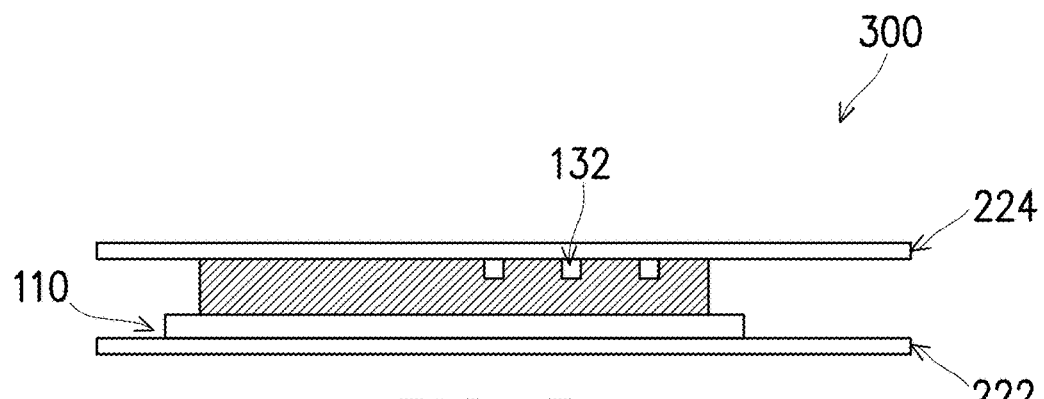
FIG. 3 illustrates another side view of an example bio-detector device along cross-section "B" annotated in FIG. 1 in accordance with various embodiments of the present disclosure.

FIG. 3 illustrates another side view 300 of an example bio-detector device along cross-section "B" annotated in FIG. 1 in accordance with various embodiments of the present disclosure.

Figure 4:
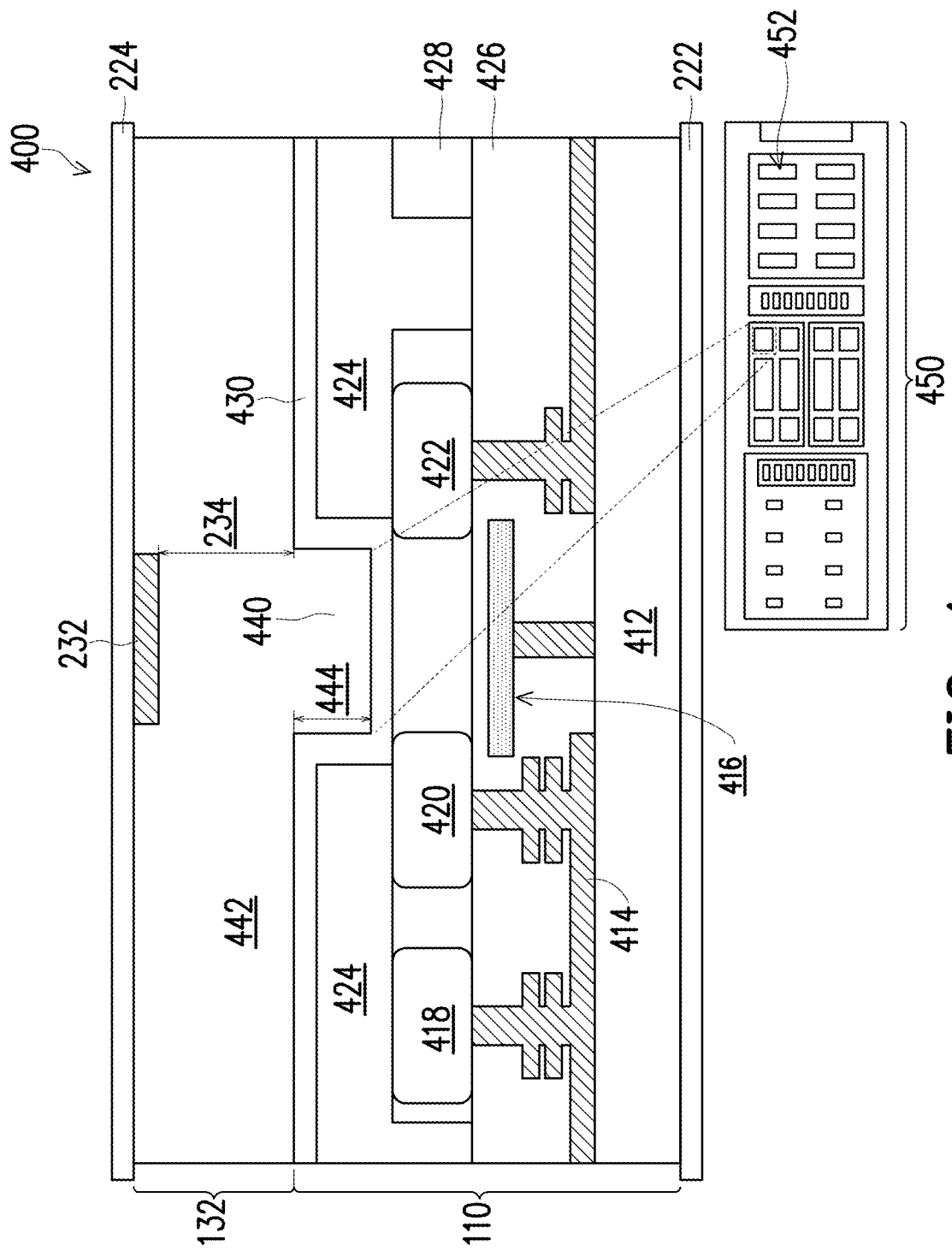
FIG. 4 illustrates an exploded side view of another example bio-detector device extracted from top view in accordance with various embodiments of the present disclosure.

FIG. 4 illustrates an exploded side view 400 of another example bio-detector device extracted from top view 450 in accordance with various embodiments of the present disclosure. In the embodiment illustrated in FIG. 4, bio-MOSFET 110 can be an ion-sensing field-effect transistor (ISFET) make up of a handling substrate 412, interconnect 414, poly gate (PG) 416, base electrode 418, source/drain terminals 420, 422, insulator layer 424, metal interconnect layer 426, silicon 428, and sensing film 430. The handling substrate 412 is coupled to the bottom layer 222. Individual interconnects 414 couple each of the base electrode 418, source/drain terminals, and PG 416 to the handing substrate 412. A metal interconnect layer 426 surrounds each of the interconnects 414 and the PG 416. The base electrode 418 and source/drain terminals 420, 422 are located within silicon 428. An insulator layer 424 such as a buried oxide layer separates the sensing film 430 from the base electrode. The sensing film 430 can be any high-k sensing film and include materials such as hafnium dioxide (HfO2), zirconium dioxide (ZrO2), and/or titanium dioxide (TiO2). The sensing film 430 forms a recess well 440 between the source/drain terminals 420, 422. The depth 444 of the recess well 440 in some embodiments can be about Top view 450 illustrates that the sizing of the recess wells such as recess well 452 can vary to facilitate detection of different sized bio-targets. A solution 442 containing a buffer and cell culture medium having the bio-target fills the channel 132 and the recess well 440. The sensing layer 430 contacts the source/drain terminals 422, 422 within the area of the recess well 440 so as to facilitate an electrical connection between the bio-MOSFET 110 and the bio-target under test.

Figure 5:
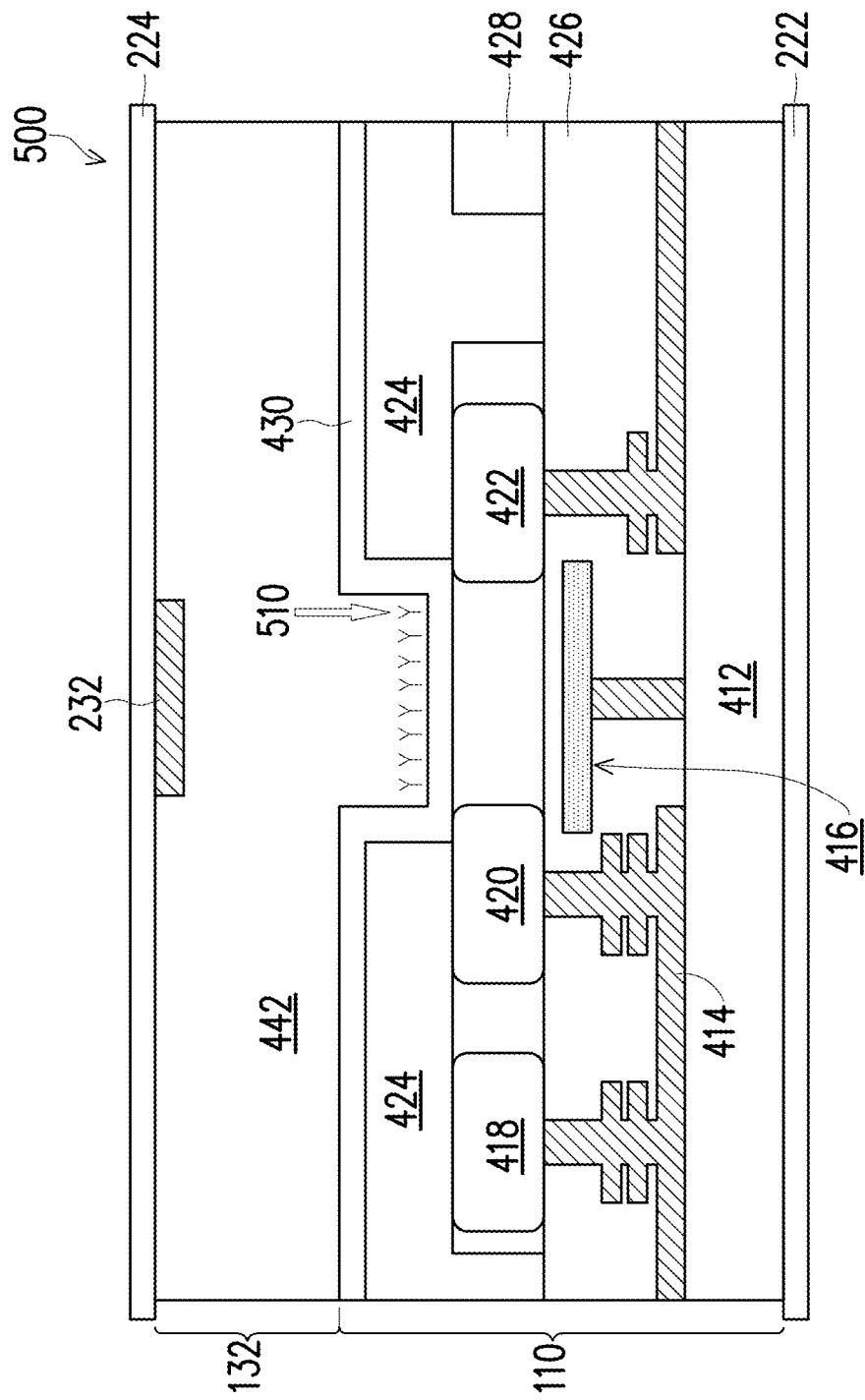
FIG. 5 illustrates a side view of another example bio-detector device having biomarkers 510 in accordance with various embodiments of the present disclosure.

FIG. 5 illustrates a side view 500 of another example bio-detector device having biomarkers 510 in accordance with various embodiments of the present disclosure. As illustrated in FIG. 5, one or more biomarkers 510 are bonded to the surface of the bio-MOSFET 110. More specifically, the one or more biomarkers 510 can bond to the sensing film 430. Biomarkers 510 can be different cell proteins that help to identify specific bio-targets within solution 442. For example, a breast cancer cell biomarker is HER2. The protein of HER2 can be bonded to the sensing film 420 within the recess well 440 and will bind with any breast cancer cells contained within solution 442. The solution 442 can be drained and the surface of the bio-MOSFET 110 can be washed with a final wash. In this example, any breast cancer cells that are bonded with biomarkers 510 will remain on the surface of the sensing film 420 within the recess well 440 and those cells within the bio-target can be identified as breast cancer cells. Although the embodiment illustrated in FIG. 5 is described in relation to breast cancer cells and corresponding biomarkers, one can appreciate that any combination of bio-targets and corresponding biomarkers can be used in connection with the bio-detector device described herein.

Figure 6:
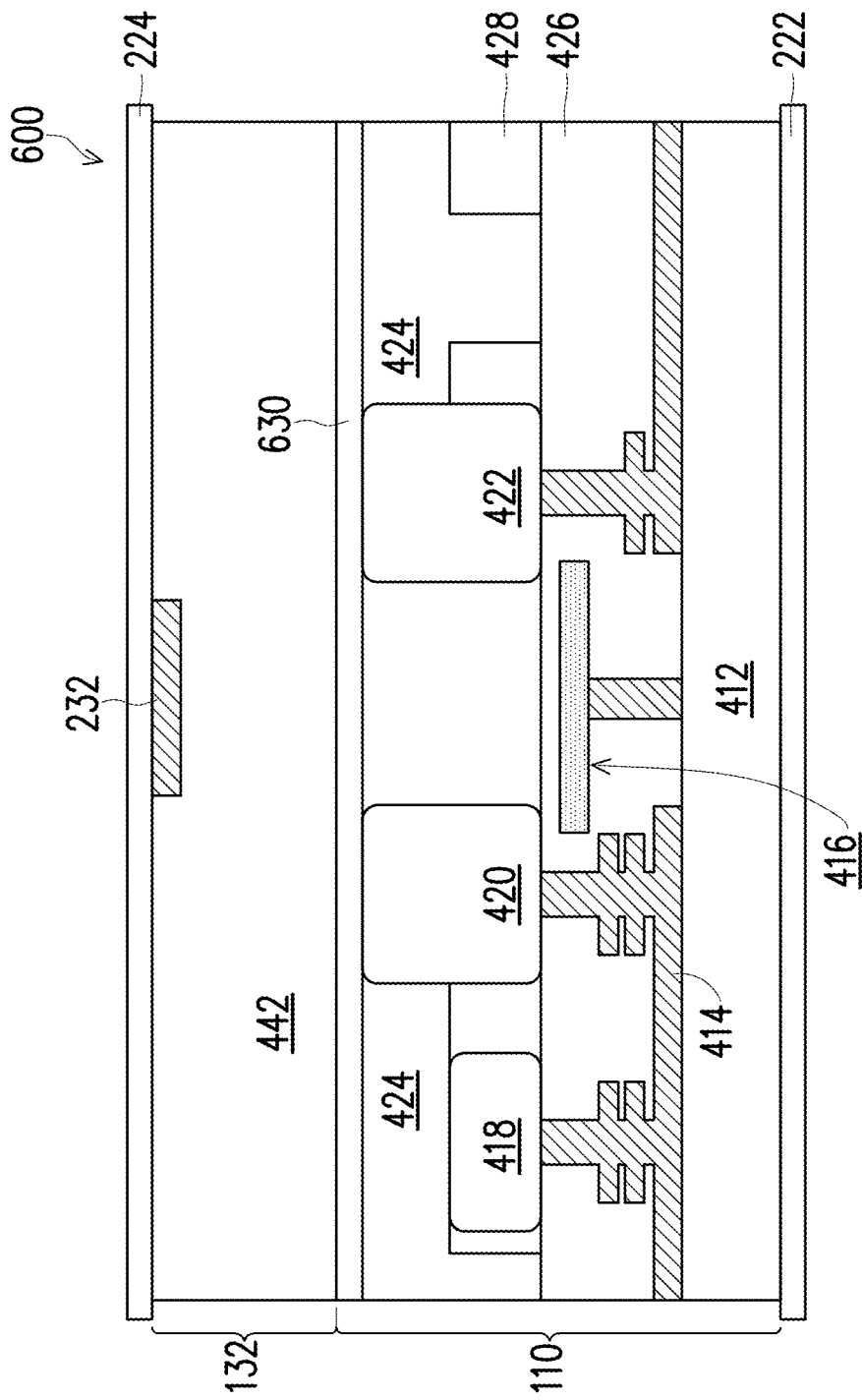
FIG. 6 illustrates a side view of another example bio-detector device in accordance with various embodiments of the present disclosure.

FIG. 6 illustrates a side view 600 of another example bio-detector device in accordance with various embodiments of the present disclosure. The bio-MOSFET 610 is structurally similar to the bio-MOSFET 110 described in FIGS. 4-5, with the exception of sensing film 630. As illustrated in FIG. 6 the sensing film 630 is planar having no recess well.

Figure 7:
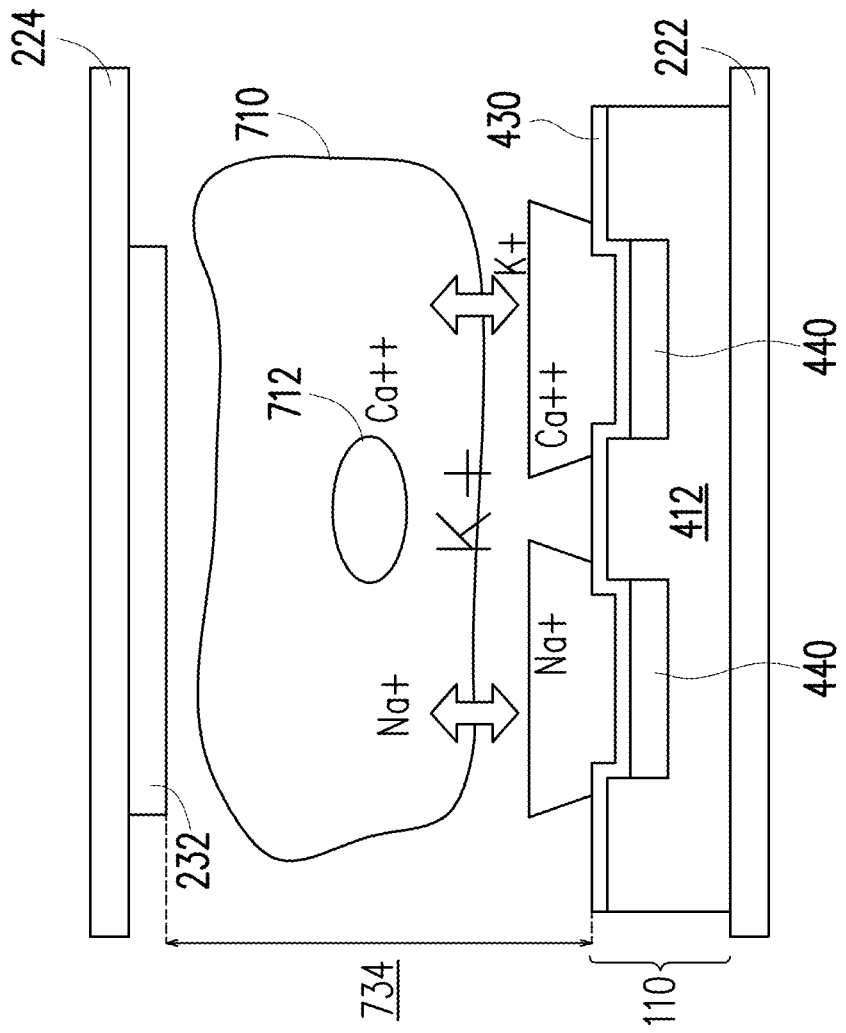
FIG. 7 illustrates an example bio-target detection using a bio-detector device in accordance with various embodiments of the present disclosure.

FIG. 7 illustrates an example bio-target detection using a bio-detector device in accordance with various embodiments of the present disclosure. For ease in understanding, the process is described with reference to structures described previously in FIGS. 4-5. But it is understood that the process applies to many other structures as well. In this example, bio-target 710 contains a cardiac cell 712. The height or distance 734 between the reference electrode 232 and a surface of the bio-MOSFET 110 (e.g., a surface of the sensing film 430) is about 2.05 mm in this example. The bio-target device illustrated in FIG. 7 can detect a presence of the cardiac cell 734 (e.g., analyte) based on the electrical properties (e.g., current) between the reference electrode 232 and bio-MOSFET 110. Cardiac cell 712 includes ions such as sodium ions ($NA^+$), potassium ions ($K^+$), and/or calcium ions ($CA^{2+}$). Any of the sodium ions ($NA^+$), potassium ions ($K^+$), and/or calcium ions ($CA^{2+}$) can transport into and/or out of the bio target 710 and detected by sensing film 430. For example, cardiac cell 712 absorbs extracellular calcium ions ($CA^{2+}$) within a human body when the human's heart beats. Those extracellular ions are shed from the cardiac cells 710 when take outside of the body (e.g., within bio-target 710 sample), the content of the extracellular calcium ions decreases as those extracellular calcium ions ($CA^{2+}$) are shed from the cardiac cell and sensed by sensing film 430. The current between the reference electrode 232 and bio-MOSFET 110 will decrease based on the presence of the extracellular calcium ions ($CA^{2+}$) on the sensing film 430.

Figure 8C:
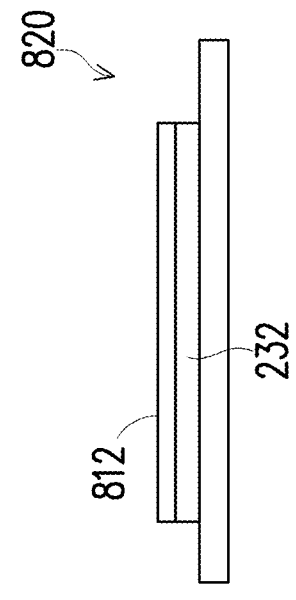
FIG. 8C illustrates a third stage of fabricating a top electrode assembly in accordance with various embodiments of the present disclosure.
Figure 8D:
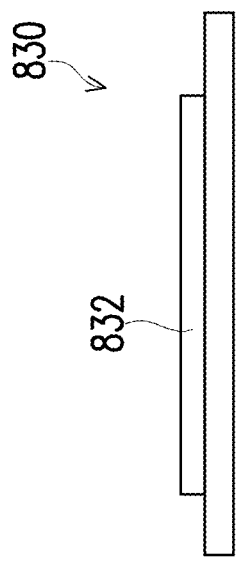
FIG. 8D illustrates a fourth stage of fabricating a top electrode assembly in accordance with various embodiments of the present disclosure.
Figure 8A:
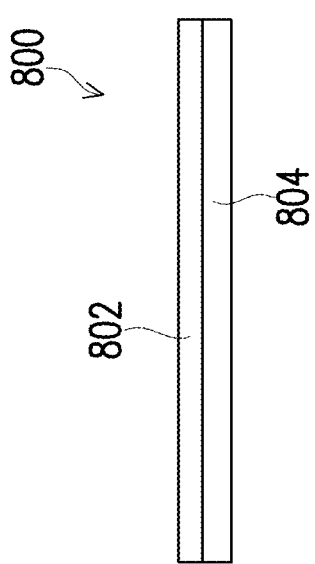
FIG. 8A illustrates a first stage of fabricating a top electrode assembly in accordance with various embodiments of the present disclosure.

FIGS. 8A-8D illustrate various stages of fabricating a top electrode assembly having top layer 224 and one or more reference electrodes 232 in accordance with various embodiments of the present disclosure. FIG. 8A illustrates a first stage 800 of fabricating a top electrode assembly in accordance with various embodiments of the present disclosure. During the first stage 800, a metal layer 802 is deposited onto a substrate 804 using, for example, sputtering deposition. Sputtering deposition is physical vapor deposition (PVD) method where a thin film is deposited onto a substrate by applying the elements in gaseous form. In some embodiments, the metal layer 802 can include materials such as gold (Au), platinum (Pt), silver (Ag), silver chloride (AgCl), or any combination thereof. The substrate 804 (e.g., top layer 224) can made up of any of a PCB, glass, acrylic, or PMMA.

Figure 8B:
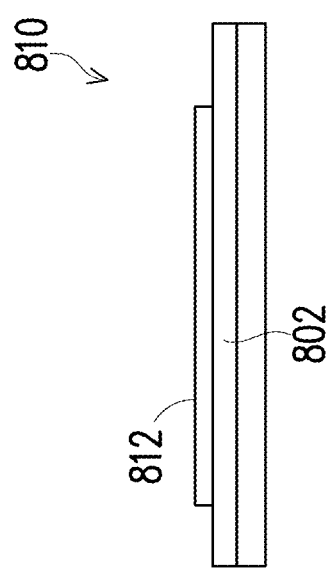
FIG. 8B illustrates a second stage of fabricating a top electrode assembly in accordance with various embodiments of the present disclosure.

FIG. 8B illustrates a second stage 810 of fabricating a top electrode assembly in accordance with various embodiments of the present disclosure. During the second stage 810, a photoresist (PR) mask is applied to the metal layer 802 in preparation for etching. The PR mask can facilitate various types of patterning of the reference electrode 232 as described in more detail in FIGS. 10-11.

FIG. 8C illustrates a third stage 820 of fabricating a top electrode assembly in accordance with various embodiments of the present disclosure. During the third stage 820, the metal layer 802 is etched using metal etching to pattern the metal layer 810 into reference electrode 232. The various dimensions resulting from this patterning during the third stage 820 are described in more detail in FIGS. 9A-9D.

FIG. 8D illustrates a fourth stage 830 of fabricating a top electrode assembly in accordance with various embodiments of the present disclosure. During the fourth stage 830, once patterning of the metal layer 810 is complete, the PR layer 812 is removed and the resultant electrode 232 formation is complete.

FIGS. 9A-9D illustrate various cross-sectional views of the references electrode 232 resulting from the fabrication process in accordance with various embodiments of the present disclosure. FIG. 9A illustrates a cross-sectional view 900 of reference electrode 232 in accordance with various embodiments of the present disclosure. Reference electrode 232 can have a length 902 ranging from 50 μm to 900 μm. FIG. 9B illustrates another cross-sectional view 910 of reference electrode 232 in accordance with various embodiments of the present disclosure. Reference electrode 232 can have a width 912 ranging from 50 μm to 900 μm. FIG. 9C illustrates another cross-sectional view 920 of reference electrode 232 in accordance with various embodiments of the present disclosure. Reference electrode 232 can have a thickness of 922 ranging between 100 μm to 2 mm.

The ratios between the thickness 922, width 912, and length 902 of the reference electrode 232 can be sized appropriately so as not to affect adhesion of the reference electrode 232 on the surface of the bio-MOSFET 110. For example, in some embodiments, the ratio between length 902 and width 912 (e.g., L:W) can be about 1:18. The ratio between length 902 and thickness 922 (e.g., L:T) can be about 1:5 in some embodiments. Similarly, the ratio between width 912 and thickness 922 (e.g., W:T) can be about 1:5.

FIG. 9D illustrates another cross-sectional view 930 of reference electrode 232 in accordance with various embodiments of the present disclosure. In this embodiment, reference electrode 232 includes a bottom layer 932, a core material 934, and an exterior layer 936. The deposition of these layers can be similar to that as previously described in FIG. 8A. The bottom layer 932 is made up of chromium (Cr). The core material 934 can be silver (Ag) or silver chloride (AgCl). The exterior layer 936 can be graphene oxide (GO).

Figure 10:
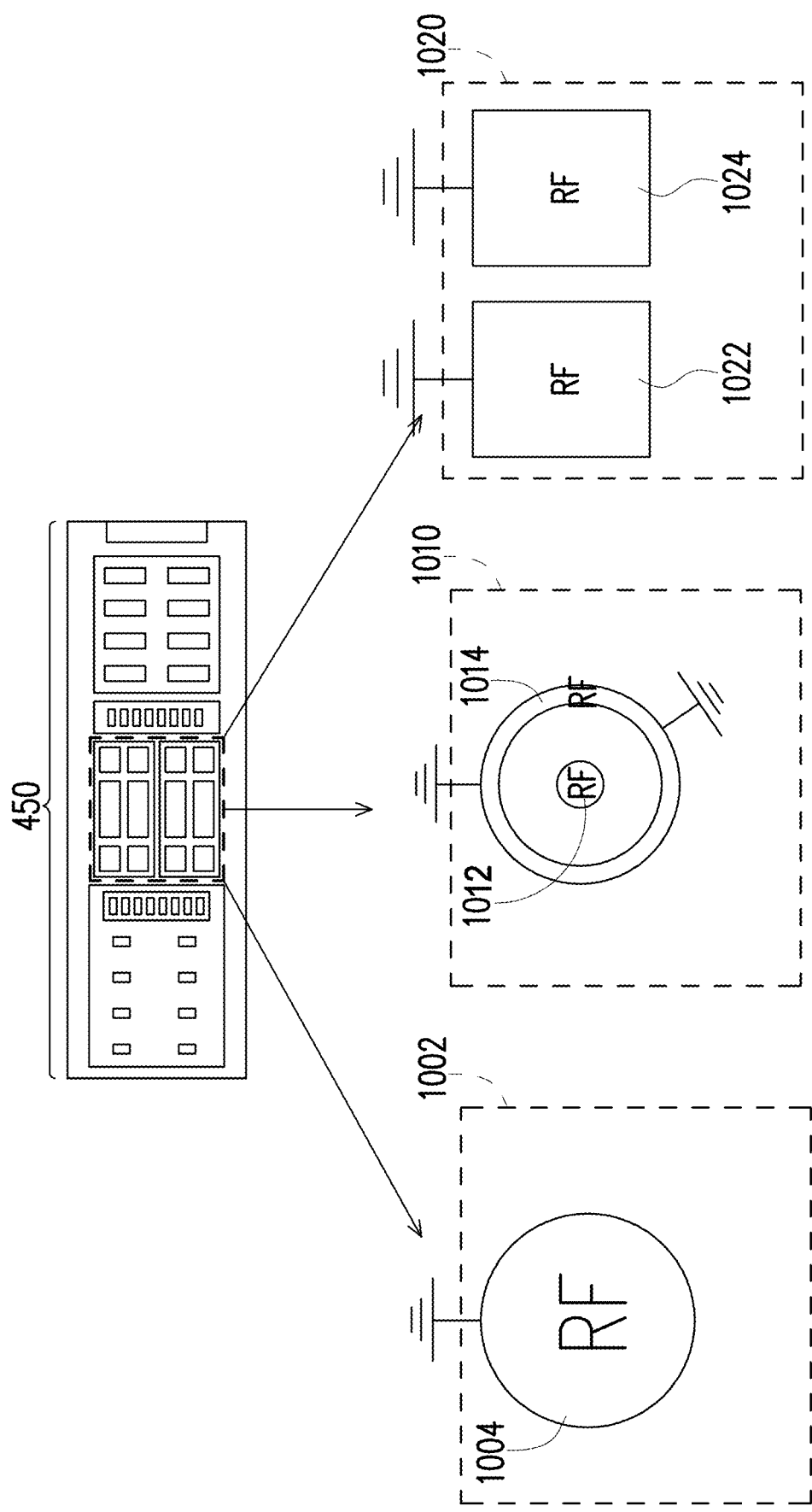
FIG. 10 illustrates exploded views of various patterns of the reference electrode from top view of an example bio-detector device in accordance with various embodiments of the present disclosure.

FIG. 10 illustrates exploded views of various patterns of the reference electrode 232 from top view 450 of an example bio-detector device in accordance with various embodiments of the present disclosure. The example bio-detector device of FIG. 10 includes a single channel having one reference electrode 232 located within the channel. With this configuration, the single reference electrode 232 is patterned in a number of ways. In one example, channel 1002 can include a single electrode 1004 patterned such that voltage is applied at a single site. In another example, channel 1010 includes a single reference electrode patterned to have two sites: inner site 1012 and outer site 1014. Voltage is applied to inner site 1012 for concentrating that voltage. Voltage is applied to the outer site 1014 to disperse the voltage throughout the reference electrode 1010. Applying voltage to both the inner site 1012 and the outer site 1014 sequentially leads to a three-dimensional (3D) rotational movement of the analytes within the bio-target being tested. In yet another example, the channel 1020 includes a single reference electrode patterned to have two side-by-side sites: left site 1022 and right site 1024. Applying voltage to the left site 1022 and the right site 1024 in sequence (e.g., left site 1022 to right site 1024), leads to two-dimensional (2D) rotation of the analytes within the bio-target being tested. Rotation of the analytes can improve molecule pairing efficiency to the sensing film.

Figure 11:
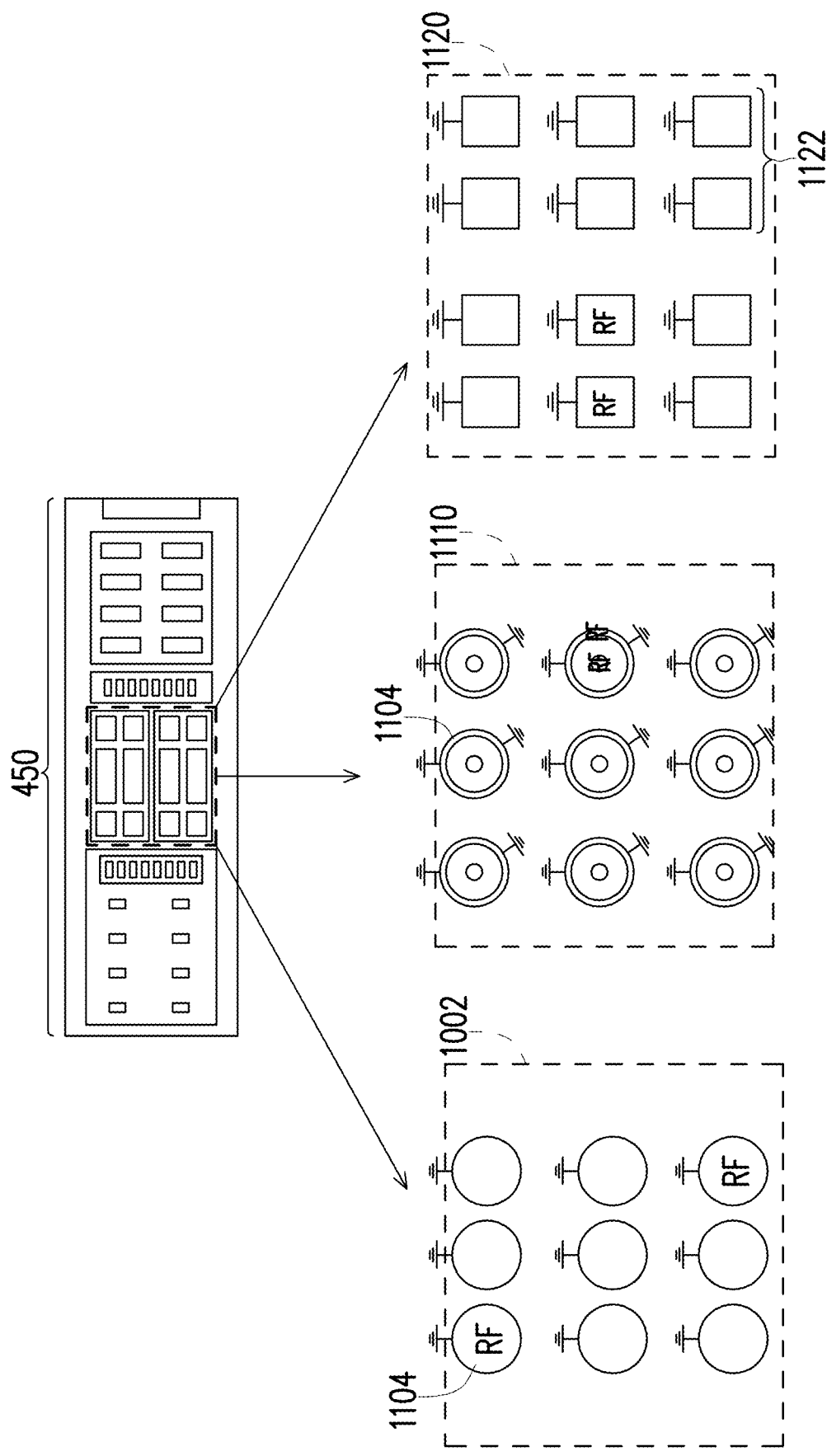
FIG. 11 illustrates exploded views of various patterns of the reference electrode from top view of an example bio-detector device in accordance with various embodiments of the present disclosure.

FIG. 11 illustrates exploded views of various patterns of the reference electrode 232 from top view 450 of an example bio-detector device in accordance with various embodiments of the present disclosure. The example bio-detector device of FIG. 11 includes a single channel having multiple reference electrodes 232 located within the channel. With this configuration, the multiple reference electrodes 232 are patterned in a number of ways, such as those described in FIG. 10. In one example, channel 1102 can include multiple reference electrodes 1104. Each reference electrode patterned such that voltage is applied at single site as described in relation to channel 1002. In another example, channel 1110 includes multiple reference electrodes 1114. Each reference electrode 1114 is patterned to have two sites as described in detail in relation to channel 1004. In yet another example, the channel 1120 includes multiple reference electrodes 1122. Each reference electrode is patterned to have two side-by-side sites as described in relation to channel 1020.

Although FIGS. 10-11 are described in relation to a single channel, it can be appreciated that multiple channels having one or more electrodes can be used for detecting analytes within a bio-target. With the use of multiple channels, chamber separation may be needed based on the type of analyte.

FIG. 12A illustrates a side view 1200 of a silicon polymer body 130 in accordance with various embodiments of the present disclosure. In some embodiments, PMMA mold is fabricated, in some embodiments, using an engraving machine. The silicon polymer body 130 is formed through molding of PDMS using the PMMA mold. FIG. 12B illustrates a top view 1210 of a silicon polymer body 130 in accordance with various embodiments of the present disclosure.

Figure 13A:
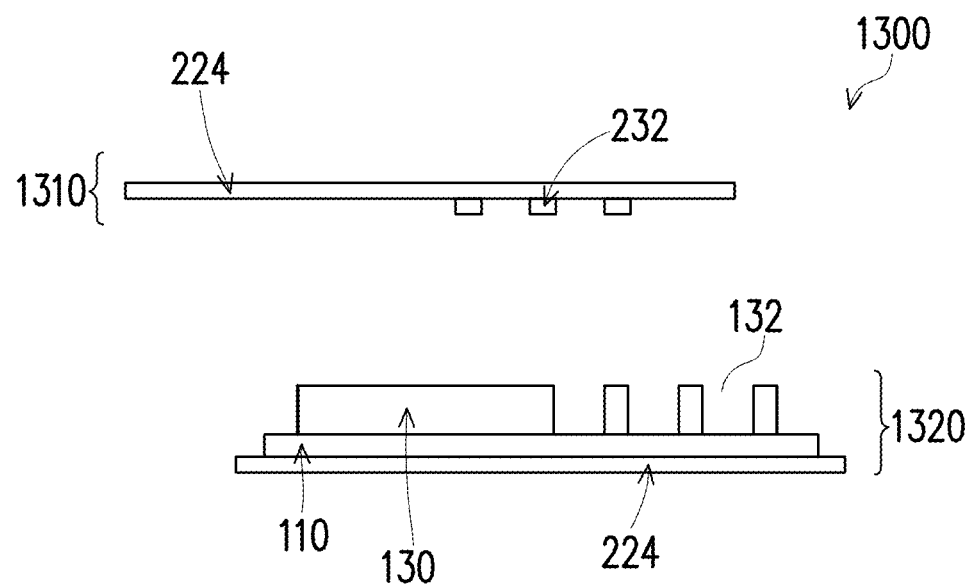
FIG. 13A illustrates a first stage of fabricating a bio detector device in accordance with various embodiments of the present disclosure.
Figure 13B:
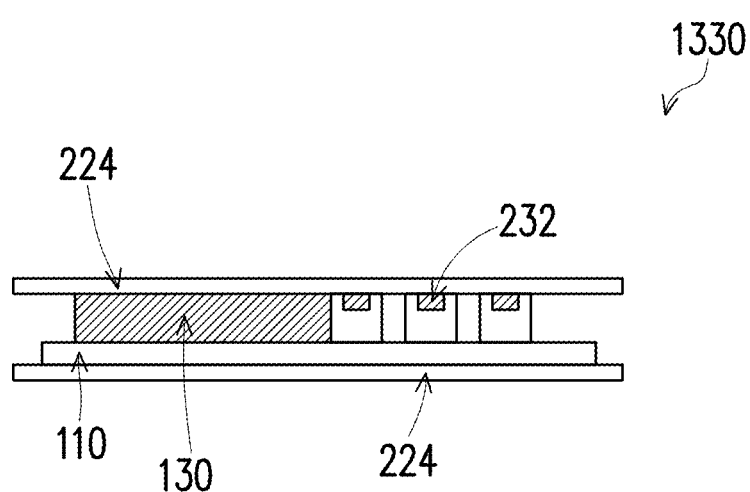
FIG. 13B illustrates a second stage of fabricating a bio detector device in accordance with various embodiments of the present disclosure.
Figure 13C:
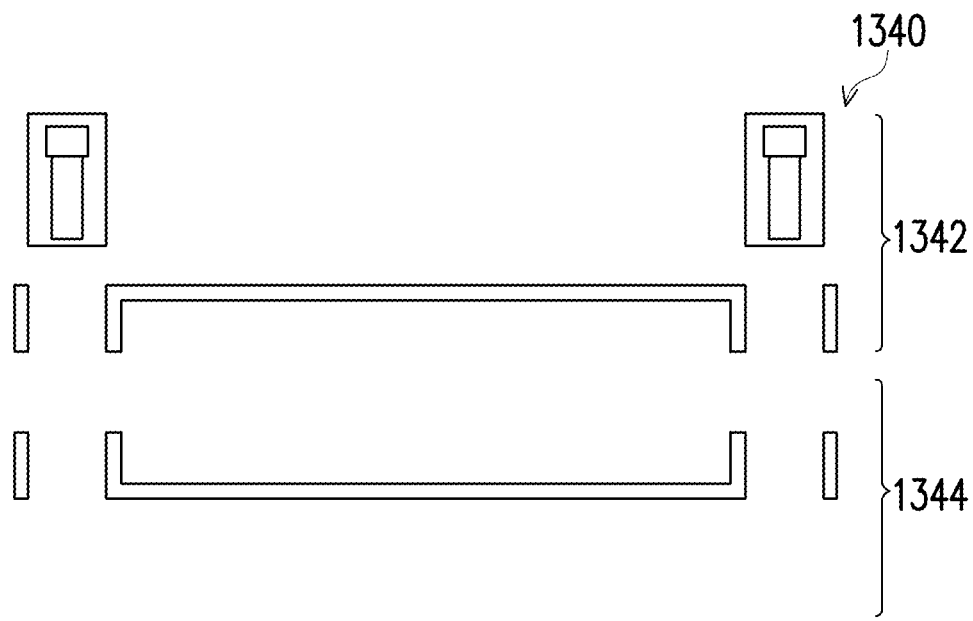
FIG. 13C illustrates a third stage of fabricating a bio detector device in accordance with various embodiments of the present disclosure.
Figure 13D:
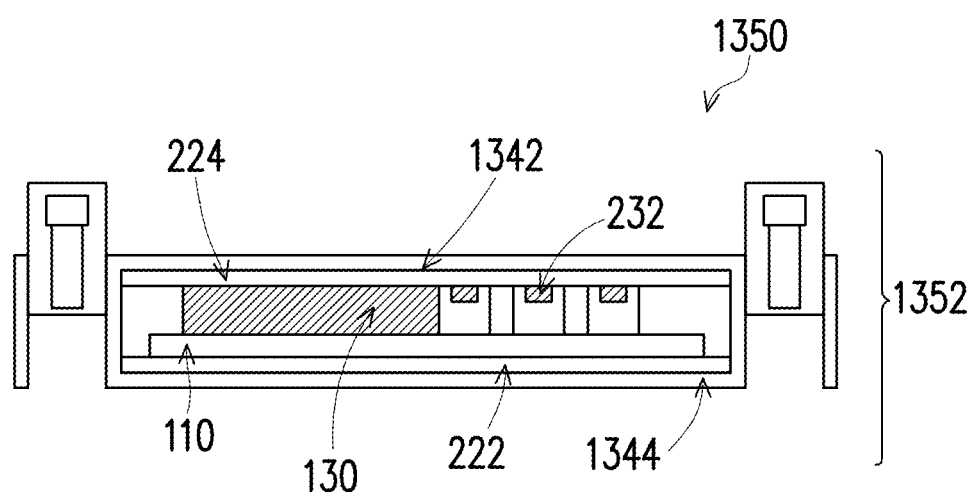
FIG. 13D illustrates a fourth stage of fabricating a bio detector device in accordance with various embodiments of the present disclosure.

FIGS. 13A-13D illustrate various stages of fabricating a bio detector device in accordance with various embodiments of the present disclosure. FIG. 13A illustrates a first stage 1300 of fabricating a bio detector device 1352 in accordance with various embodiments of the present disclosure. In a first stage 1300, two separate assemblies are fabricated. A top electrode assembly 1310 is fabricated as described in detail in FIGS. 8A-8D. As previously described, the top electrode assembly 1310 includes a top layer 224 and one or more reference electrodes 232. A bottom chip assembly 1320 is fabricated by disposing the bio-MOSFET chip 110 described in detail in FIGS. 4-6 on a bottom layer 222. A silicon polymer body 130, fabricated as previously described in FIGS. 12A-12B, are disposed onto bio-MOSFET chip 110. FIG. 13B illustrates a second stage 1330 of fabricating a bio detector device 1352 in accordance with various embodiments of the present disclosure. During a second stage 1330, the top electrode assembly 1310 and bottom electrode assembly 1320 are assembled together. FIG. 13C illustrates a third stage 1340 of fabricating a bio detector device 1352 in accordance with various embodiments of the present disclosure. During a third stage 1340, an upper cover (e.g., PMMA module) and a lower lid (e.g., PMMA module) are fabricated using a laser engraving machine. FIG. 13D illustrates a fourth stage 1350 of fabricating a bio detector device 1352 in accordance with various embodiments of the present disclosure. During a fourth stage 1350, the assembled together top electrode assembly 1310 and bottom chip assembly 1320 are encased within the upper cover 1342 and lower lid 1344 to form the bio detector 1352.

Figure 14:
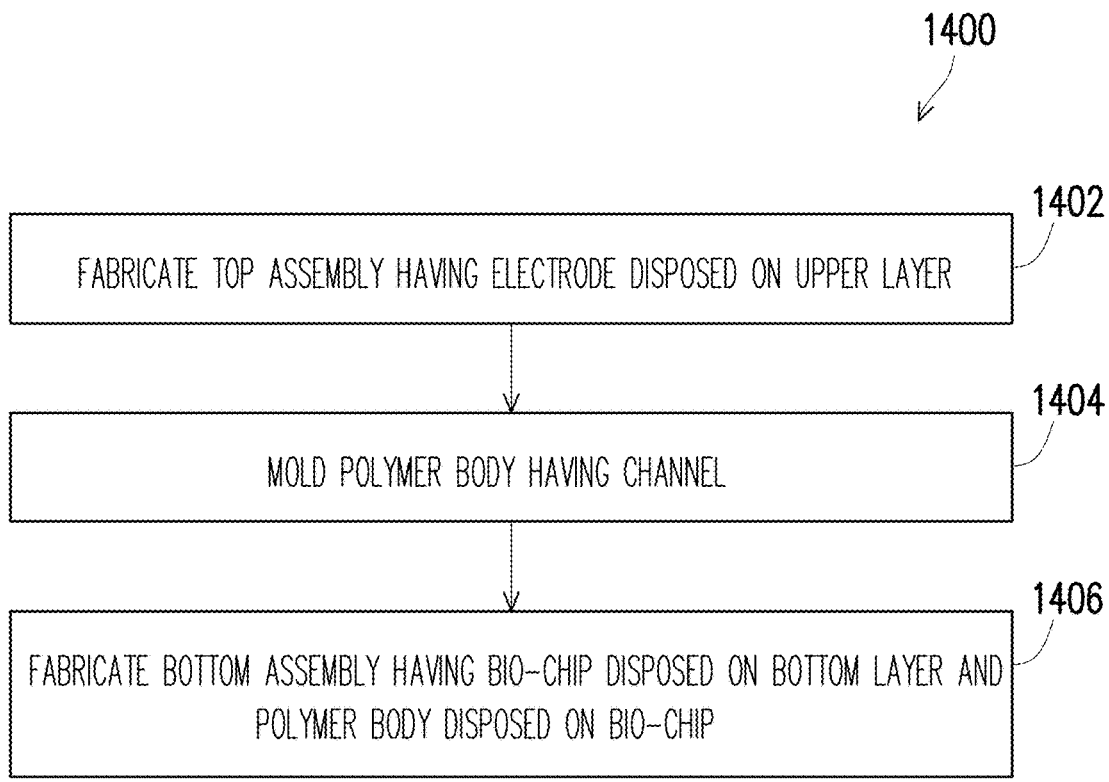
FIG. 14 illustrates an exemplary flow diagram process for fabricating a bio-detector device in accordance with various embodiments of the present disclosure.

FIG. 14 illustrates an exemplary flow diagram 1400 process for fabricating a bio-detector device 1352 in accordance with various embodiments of the present disclosure. For ease in understanding, the process is described with reference to structures described previously herein. But it is understood that the process applies to many other structures as well. In step 1402, a top assembly is fabricated as previously described in detail in FIGS. 8A-8D. In step 1404, a silicon polymer body 132 is molded as previously described in detail in FIGS. 12A-12B. In step 1406, a bottom assembly is fabricated as described in detail in FIGS. 13A-13D.

Figure 15:
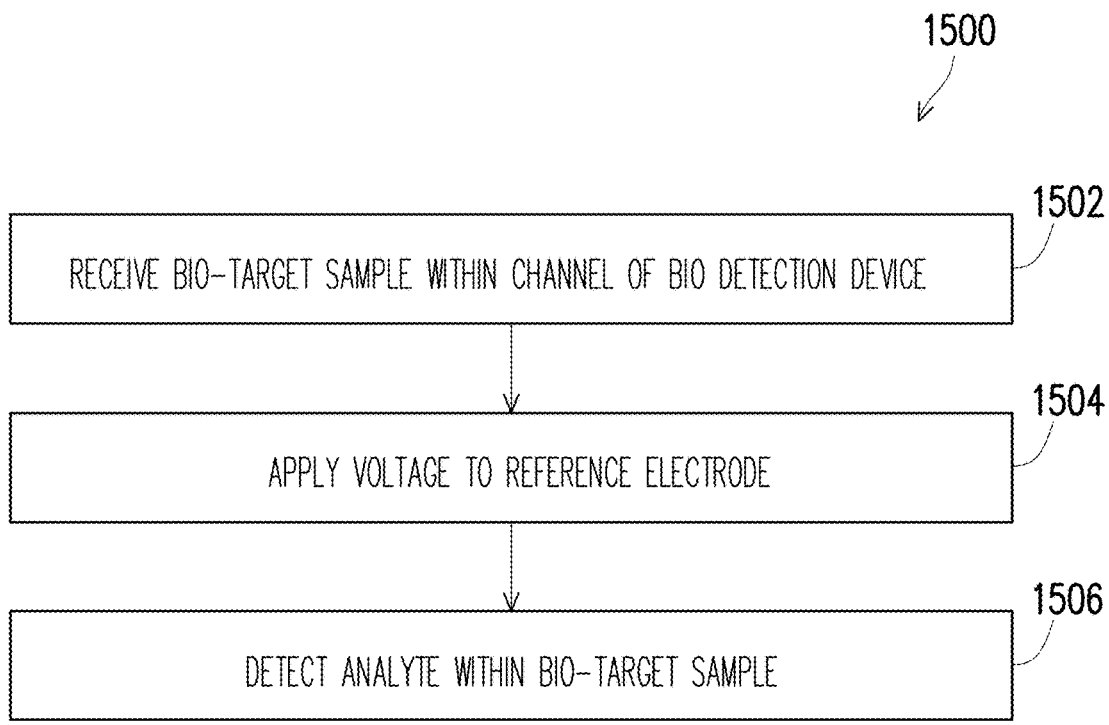
FIG. 15 illustrates an exemplary flow diagram for detecting an analyte using a bio detection device in accordance with various embodiments of the present disclosure.

FIG. 15 illustrates an exemplary flow diagram 1500 for detecting an analyte using a bio detection device 1352 in accordance with various embodiments of the present disclosure. For ease in understanding, the process is described with reference to structures described previously herein. But it is understood that the process applies to many other structures as well. In step 1502, a bio-target (e.g., bio-target 710) having the analyte (e.g., cardiac cell 712) is received within a channel 132 of a polymer body 130 in the bio detection device 1352. A voltage is applied, during step 1504, to a reference electrode 232 of the bio-detection device 1352. For example, voltage can be applied in the various ways discussed in detail in FIGS. 10-11. The analyte (e.g., cardiac cell 712) within the bio-target (e.g., bio-target 710) is detected based on current between the reference electrode 232 and a bio-chip 110 of the bio-detection device 1352. The bio-detection device can be any of those described in detail in FIGS. 4-7 and 13D.

Use of the bio-detectors as described herein can provide a number of advantages in embodiments. For example, the bio-detector integrated with electrode and bio-MOSFET chip has the advantages of high precision and throughput along with small size and low costs, which makes it suitable for portable point-of-care diagnostics. The design of the integrated detector device allows modification or adjustment of the distance between RF electrode and sensing surface of bio-MOSFET chip in the reservoir of the PDMS body, such flexible design makes it suitable for detecting bio-targets of various sizes in diagnostic analysis. For example, for the diagnostic analysis of various sizes of bio-targets, the distance between an electrode and bio-MOSFET chip surface can be adjusted such that it is large enough to allow analytes of a specific size pass through. Use of the bio-detectors as described herein can obviate the need for cell staining and labeling as cell identification can be performed through modification on a sensor surface with paired molecules.

In one embodiment, a device for detecting an analyte within a bio-target includes a top assembly and a bottom assembly. The top assembly includes an electrode disposed on a top layer. The bottom assembly includes a bio-chip disposed on a bottom layer and a polymer body disposed between the bio-chip and the top assembly. The polymer body includes a channel. The electrode is positioned within the channel. The channel configured to accommodate the bio-target containing the analyte.

In another embodiment, a method of fabricating a device for detecting an analyte within a bio-target includes fabricating a top assembly having an electrode disposed on an upper layer, molding a polymer body having a channel, and fabricating a bottom assembly having a bio-chip disposed on a bottom layer. The top assembly, the bottom assembly, and the polymer body are assembled together with the polymer body between the top assembly and the bottom assembly. The electrode is positioned within the channel and the channel is configured to accommodate the bio-target comprising the analyte.

In yet another embodiment, a method of detecting an analyte using a bio detection device, the method includes receiving a bio-target having the analyte within a channel of a polymer body in the bio detection device. A voltage is applied to a reference electrode of the bio-detection device. The analyte is detected within the bio-target based on current between the reference electrode and a bio-chip of the bio-detection device. The bio-detection device includes a top assembly having an electrode disposed on a top layer, a bottom assembly including a bio-chip disposed on a bottom layer and a polymer body disposed between the bio-chip and the top assembly. The polymer body includes a channel and the electrode is positioned within the channel.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A device for detecting an analyte within a bio-target, the device comprising:
   a top assembly comprising a plurality of electrodes disposed on a top layer; and
   a bottom assembly comprising a bio-chip disposed on a bottom layer and a polymer body disposed between the bio-chip and the top assembly, wherein the polymer body includes a channel having the one or more electrodes of the plurality of electrodes positioned within, wherein the one or more electrodes and the bio-chip are disposed at opposite sides of the channel, wherein the channel configured to accommodate the bio-target comprising the analyte and wherein an electrode of the plurality of electrodes is configured to enable rotation of the analyte based on an application of first and second voltages in sequence.

2. The device of claim 1, wherein a size of the analyte fits within a height of the channel and the height is measured from a surface of the electrode within the channel and a top surface of the bio-chip.

3. The device of claim 1, wherein the height of the channel is between 2.0 mm and 3.0 mm and is variable based on a thickness of the electrode or a thickness of the polymer body.

4. The device of claim 1, wherein one or more biomarkers are bonded to a surface of the bio-chip within the channel, the one or more biomarkers comprising a protein associated with the analyte.

5. The device of claim 1, wherein the bio-chip comprises:
   a semiconductor substrate;
   a source and a drain embedded in the semiconductor substrate;
   a channel layer disposed between the source and the drain; and
   a sensing dielectric layer disposed over the semiconductor substrate and above the channel layer.

6. The device of claim 5, wherein the bio-chip is an ion sensitive field effect transistor (IS-FET) and the sensing dielectric layer is an ion sensitive dielectric layer.

7. The device of claim 5, wherein the sensing dielectric layer comprises at least one of hafnium dioxide ($HfO_2$), zirconium dioxide ($ZrO_2$), or titanium dioxide ($TiO_2$).

8. The device of claim 1, wherein the electrode comprises at least one of platinum (Pt), gold (Au), silver (Ag), or silver chloride (AgCl).

9. The device of claim 1, wherein the top layer comprises at least one of a printed circuit board (PCB), glass, acrylic, or Poly(methyl methacrylate) (PMMA) and the bottom layer comprises PCB.

10. The device of claim 1, wherein a width of the electrode is between 50 μm and 900 μm, a length of the electrode is between 50 μm and 900 μm, and a thickness of the electrode is between 100 μm and 2 mm.

11. The device of claim 10, wherein a ratio between the length and the width of the electrode is 1:18, wherein a second ratio between the length and the thickness of the electrode is 1:5.

12. The device of claim 1, wherein the electrode is patterned to have an inner site configured to receive a first voltage and an outer site configured to receive a second voltage, and wherein the electrode enables three-dimensional rotation of the analyte based on a sequential application of the first voltage and the second voltage.

13. The device of claim 1, wherein the electrode is pattered to have a left site configured to receive a first voltage and a right site configured to receive a second voltage, and wherein the electrode enables two-dimensional rotation of the analyte based on a sequential application of the first voltage and the second voltage.

14. A method of fabricating a device for detecting an analyte within a bio-target, the method comprising:
   fabricating a top assembly having an electrode disposed on an upper layer;
   molding a polymer body having a channel; and
   fabricating a bottom assembly comprising a bio-chip disposed on a bottom layer;
   assembling together the top assembly, the bottom assembly, and the polymer body, wherein the polymer body is between the top assembly and the bottom assembly and wherein the electrode is positioned within the channel and the channel configured to accommodate the bio-target comprising the analyte.

15. The method of claim 14, wherein a size of the analyte fits within a height of the channel and the height is measured from a surface of the electrode within the channel and a top surface of the bio-chip.

16. The method of claim 15, further comprising adjusting a height of the channel by either fabricating the electrode to have a first thickness or molding the polymer body to have a second thickness.

17. The method of claim 14, wherein fabricating the top assembly comprises:
   depositing a metal layer onto the top layer;
   applying a photoresist layer onto the metal layer;
   patterning the metal layer using metal etching; and
   removing the photoresist layer from the metal layer.

18. The method of claim 14, wherein molding the polymer body comprises:
    fabricating a Poly(methyl methacrylate) (PMMA) mold having a plurality of channels; and
    molding the polymer body using the PMMA mold.

19. The method of claim 14, further comprising:
    fabricating an upper Poly(methyl methacrylate) (PMMA) module and a lower PMMA module; and
    encapsulating the top assembly, the polymer body, and the bottom assembly between the upper PMMA module and the lower PMMA module.

20. A method of detecting an analyte using a bio detection device, the method comprising:
    receiving a bio-target having the analyte within a channel of a polymer body in the bio detection device;
    applying a voltage to a reference electrode of the bio-detection device; and
    detecting the analyte within the bio-target based on current between the reference electrode and a bio-chip of the bio-detection device,
    wherein the bio-detection device comprises:
        a top assembly comprising an electrode disposed on a top layer; and
        a bottom assembly comprising a bio-chip disposed on a bottom layer and a polymer body disposed between the bio-chip and the top assembly, wherein the polymer body includes a channel and the electrode is positioned within the channel.

\* \* \* \* \*